(12) United States Patent
Kwon et al.

(10) Patent No.: US 8,865,762 B2
(45) Date of Patent: Oct. 21, 2014

(54) METHOD FOR THE TREATMENT OF BONE DISEASES COMPRISING COLFORSIN DAROPATE

(75) Inventors: Byoung Mog Kwon, Daejeon (KR); Dong Cho Han, Daejeon (KR); Myung Ae Bae, Daejeon (KR); Seong Hwan Kim, Daejeon (KR); Yong Ki Min, Daejeon (KR)

(73) Assignees: Korea Research Institute of Bioscience and Biotechnology, Daejeon (KR); Korea Research Institute of Chemical Technology, Daejeon (KR)

( * ) Notice: Subject to any disclaimer, the term of this patent is extended or adjusted under 35 U.S.C. 154(b) by 100 days.

(21) Appl. No.: 13/384,560

(22) PCT Filed: Jul. 16, 2010

(86) PCT No.: PCT/KR2010/004672
§ 371 (c)(1),
(2), (4) Date: Mar. 23, 2012

(87) PCT Pub. No.: WO2011/008052
PCT Pub. Date: Jan. 20, 2011

(65) Prior Publication Data
US 2012/0184604 A1    Jul. 19, 2012

(30) Foreign Application Priority Data
Jul. 17, 2009 (KR) .................. 10-2009-0065505

(51) Int. Cl.
*A61K 31/35* (2006.01)
*A61K 31/352* (2006.01)
*A23L 1/30* (2006.01)

(52) U.S. Cl.
CPC ............. *A61K 31/352* (2013.01); *A61K 31/35* (2013.01); *A23L 1/30* (2013.01)
USPC ......................................... 514/455

(58) Field of Classification Search
CPC ............................ A61K 31/35; A61K 31/352
USPC ......................................... 514/455
See application file for complete search history.

(56) References Cited

FOREIGN PATENT DOCUMENTS

WO      WO 0021523 A1 *  4/2000
WO      2008/141189      11/2008

OTHER PUBLICATIONS

Hayashida et al., "Antiinflammatory effects of colforsin daropate hydrochloride, a novel water-soluble forskolin derivative," *Ann Thorac Surg* 71:1931-1938, 2001.
Hibino et al., "Cardiovascular effects of colforsin daropate hydrochloride for acute heart failure after open heart surgery," *Kyobu Geka* 54(12):1016-1019, 2001 (abstract only).
Lee et al., "Signal transduction by receptor activator of nuclear factor kappa B in osteoclasts," *Biochemical and Biophysical Research Communications* 305:211-214, 2003.
Pittenger et al., "Multilineage Potential of Adult Human Mesenchymal Stem Cells," *Science* 284:143-147, 1999.
Uchida et al., "Both Milrinone and Colforsin Daropate Attenuate the Sustained Pial Arteriolar Constriction Seen After Unclamping of an Abdominal Aortic Cross-Clamp in Rabbits," *Anesth Analg* 101:9-16, 2005.

\* cited by examiner

*Primary Examiner* — Kevin E Weddington
(74) *Attorney, Agent, or Firm* — Seed IP Law Group PLLC

(57) ABSTRACT

The present invention relates to a pharmaceutical composition for the prevention or treatment of bone diseases comprising colforsin daropate, and more particularly, the present invention relates to a pharmaceutical composition for the prevention or treatment of bone diseases such as bone fracture and osteoporosis, which inhibits osteoclast differentiation and bone resorption caused by osteoclasts and promotes osteoblast differentiation and the activity of osteoblasts, and a health functional food composition comprising colforsin daropate.

5 Claims, 4 Drawing Sheets

Figure 3
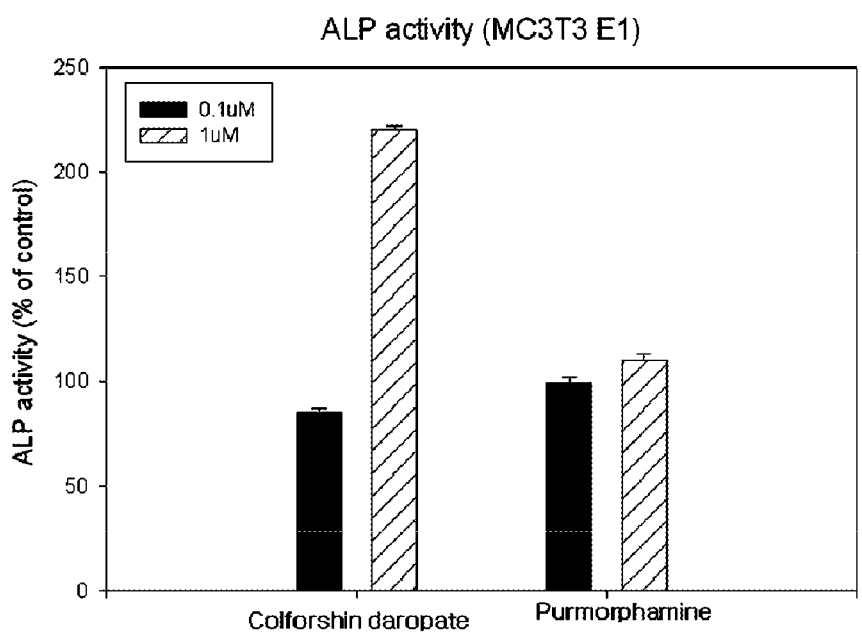
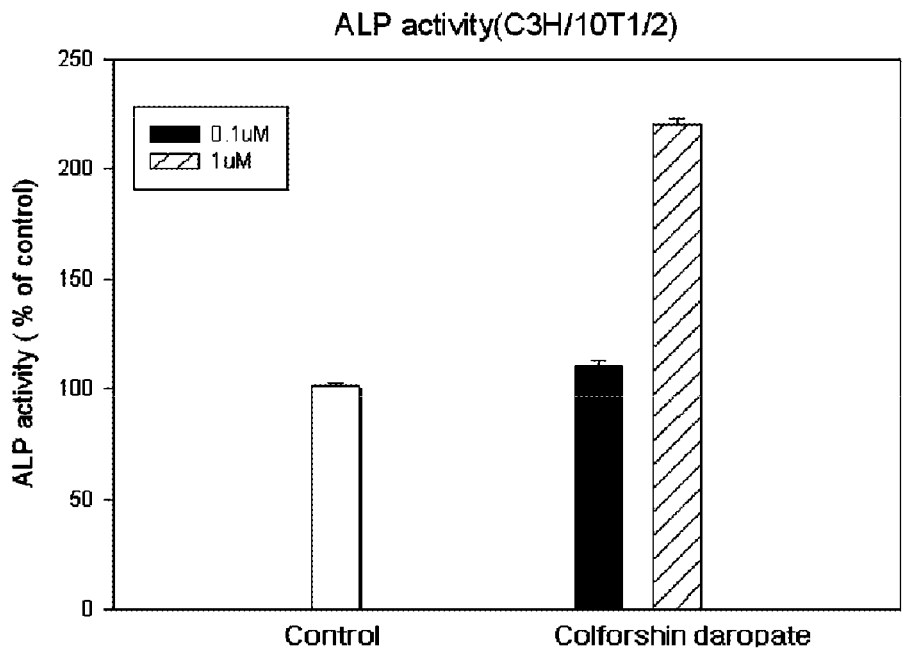

Figure 4
A
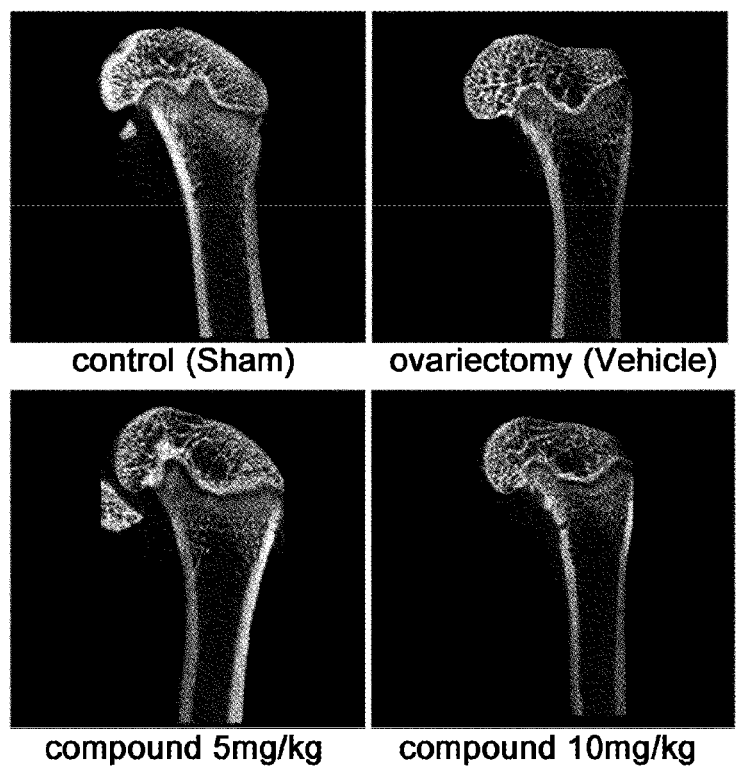
B
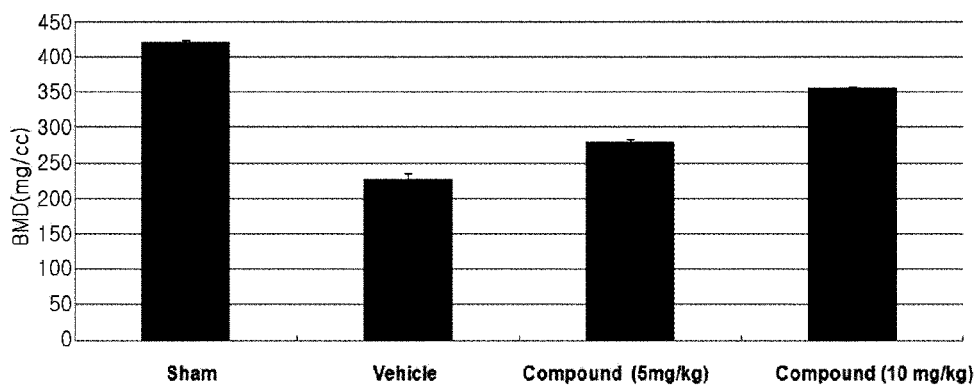

METHOD FOR THE TREATMENT OF BONE DISEASES COMPRISING COLFORSIN DAROPATE

TECHNICAL FIELD

The present invention relates to a pharmaceutical composition for the prevention or treatment of bone diseases comprising colforsin daropate, and more particularly, the present invention relates to a pharmaceutical composition for the prevention or treatment of bone diseases such as bone fracture and osteoporosis, which inhibits osteoclast differentiation and bone resorption caused by osteoclasts and promotes osteoblast differentiation and the activity of osteoblasts, and a health functional food composition comprising colforsin daropate.

BACKGROUND ART

Osseous tissue constitutes cartilage and the skeletal system, and has a mechanical function as a support and a site of muscle attachment, the functions of protecting vital organs and bone marrow, and the function of reserving ions, especially calcium and phosphate, for the maintenance of their homeostasis. Osseous tissue that functions as such is made up of a cell matrix such as collagen and proteoglycan, and various cells such as osteoblasts, osteoclasts, and osteocytes. Among them, osteoclasts are derived from hematopoietic stem cells and are responsible for the resorption of aged bone, and osteoblasts are derived from bone marrow stromal cells and are responsible for bone formation.

The murine monocytic cell line, RAW264.7 differentiates into multinucleated osteoclasts upon exposure to RANKL (receptor activator of nuclear factor κB (RANK) ligand). This differentiation is mediated by the binding of RANKL to the extracellular RANK domain to promote the activation of mitogen-activated protein kinase (MAPK), and in turn the translocation of transcription factor NF-κB into the nucleus to increase expression of osteoclast differentiation-related TRAP (tartrate-resistant acid phosphatase), MMP-9 (matrix metalloproteinase-9), and c-Src tyrosine kinase. The multinucleated osteoclasts formed during this differentiation function to resorb mineralized bone. In addition, the binding of RANKL to RANK promotes the activity of TRAF6 (tumor necrosis factor receptor-associated factor 6), leading to the activation of MAPK or transcription factors such as NF-κB, AP-1, and NFATc1 (Lee Z H, Kim H H. Signal transduction by receptor activator of nuclear factor kappa B in osteoclasts. Biochem Biophys Res Commun. 2003 May 30, 305, 211-4). Therefore, inhibition of the RANK/RANKL signal transduction pathway has been suggested as a promising approach for the treatment of bone diseases including osteoporosis.

Meanwhile, osteoblast cells are derived from mesenchymal stem cells, and mineralization such as calcium formation by osteoblast differentiation maintains bone integrity, which has an important role in the calcium and hormone homeostasis of the body. Calcium formation by osteoblast differentiation is controlled by vitamin D, parathyroid hormone or the like, and bone formation by the osteoblast differentiation is accomplished by synthesizing alkaline phosphatase (ALP) associated with osteoblast differentiation in the early stage by cross-talking between various signal transducers such as bone morphogenetic protein (BMP), Wnt, MAP kinase, calcineurin-calmodulin kinase, NF-κB and AP-I in the cell, followed by synthesizing mineralization-related elements such as osteopontin, osteocalcin, and type I collagen (Pittenger, M. F.; Mackay, A. M.; Beck, S. C.; Jaiswal, R. K.; Douglas, R.; Mosca, J. D.; Moorman, M. A., Simmonetti, D. W.; Craig, S.; Marshak, D. R. Multilineage Potential of Adult Human Mesenchymal Stem Cells. Science 1999, 284, 143-147). Therefore, since compounds stimulating alkaline phosphatase activity promote osteocyte differentiation, they can be developed as a therapeutic agent for bone diseases.

The growth of bone is controlled by bone remodeling which maintains a balance between the actions of bone resorption by osteoclast and bone formation by osteoblast. However, over-activation of the osteoclast or reduced activation of the osteoblast causes an imbalance in the bone remodeling cycle to disrupt the balance between osteoclasts and osteoblasts in the body, leading to bone diseases.

A representative bone disease, osteoporosis occurs when the balance between bone formation and bone resorption is disrupted, and thus bone resorption occurs at a higher rate, leading to loss of bone density. In the United States, nearly 10 million people already have osteoporosis. Another 18 million people have low bone mass that places them at an increased risk for developing osteoporosis. One in two women and one in eight men are predicted to have an osteoporosis-related fracture in their lifetime, and about 2 million men in the United States already have osteoporosis. The annual direct healthcare costs for osteoporosis-related disease and bone fractures are estimated to be 14 billion dollars in the United States. In Korea, approximately 4 million people either already have osteoporosis or are at a risk for this disease, and the numbers are expected to skyrocket with today's aging population. This will impose enormous social, psychological, and economic burdens on individuals.

For the treatment of bone disease, the balance between osteoclasts and osteoblasts should be controlled, and current drugs to this end include bone resorption inhibitors and bone formation stimulators. Of them, bone formation stimulators have been actively studied, but enhancement of bone density by bone formation stimulators does not always lead to reduced bone fracture. Further studies are still needed regarding its clinical applications. Moreover, a drug for stimulating bone formation should have a low toxicity and be administered orally, because stimulators for activating osteoblasts and inhibitors for inhibiting bone resorption of osteoclasts should be administered to patients for a long period of time. Accordingly, there is an urgent need to study the drug.

DISCLOSURE

Technical Problem

The present inventors have made an effort to develop a pharmaceutical composition for the prevention or treatment of bone diseases that are caused by an imbalance between osteoclasts and osteoblasts in the bone remodeling mechanism. As a result, it was found that colforsin daropate shows a therapeutic effect on bone diseases by maintaining the balance between osteoblasts and osteoclasts, thereby completing the present invention.

Technical Solution

An object of the present invention is to provide a pharmaceutical composition for the prevention or treatment of bone diseases, comprising colforsin daropate.

Another object of the present invention is to provide a method for treating bone diseases, comprising the step of administering the pharmaceutical composition to an individual.

Still another object of the present invention is to provide a health functional food composition for the prevention or amelioration of bone diseases, comprising colforsin daropate.

Advantageous Effects

The pharmaceutical composition including colforsin daropate according to the present invention effectively inhibits differentiation and bone resorption of osteoclasts, and promotes osteoblast differentiation and mineralization, thereby enhancing bone formation. Thus, the composition can be used for the prevention and treatment of bone diseases including osteoporosis.

DESCRIPTION OF DRAWINGS

FIG. 3 is a graph showing the effect of colforsin daropate on the osteoblast differentiation marker, ALP activity (A: MC3T3-E1 cell, B: C3H/10T1/2); and FIG. 4 shows the photograph of high resolution in-vivo micro-CT system (A) and the quantitative graph (B) to analyze the bone density-improving effect of colforsin daropate of the present invention in ovariectomy-induced osteoporosis models.

BEST MODE

In one embodiment to achieve the above objects, the present invention relates to a composition for the prevention or treatment of bone diseases comprising colforsin daropate, and preferably a composition for the prevention or treatment of bone diseases comprising a compound represented by Chemical Formula 1 below or a pharmaceutically acceptable salt thereof.

As used herein, "colforsin daropate" is (+)-(3R,4aR,5S,6S, 6aS,10S,10aR,10bS-5-acetoxyl-6-(3-dimethylaminopropionyloxy)-dodecahydro-10,10b-dihydroxy-3,4a,7,7,10a-pentamethyl-3-vinyl-1H-naphtho[2,1-b]pyran-1-one monohydrochloride, and has a molecular formula of $C_{27}H_{44}ClNO_8$ and a molecular weight of 546.09316 (g/mol), and is represented by the following Chemical Formula 1.

[Chemical Formula 1]

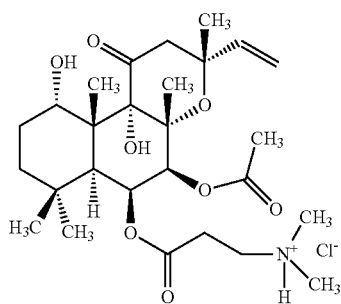

Figure 1:
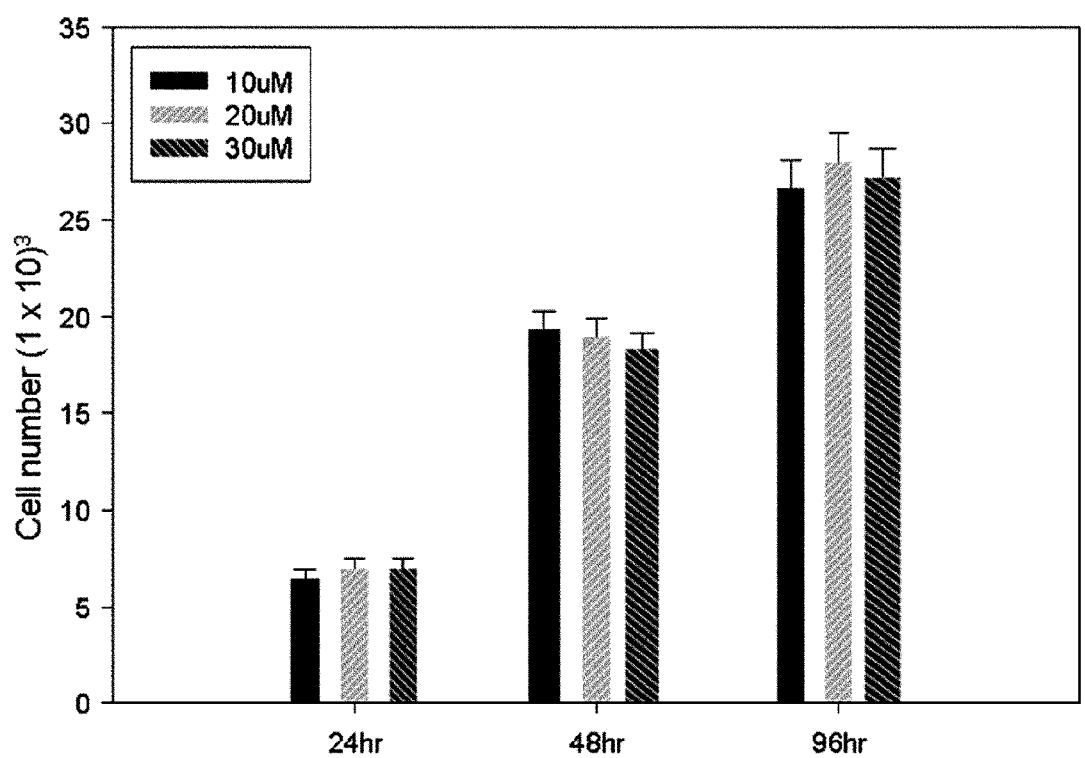
FIG. 1 is a graph showing the effect of colforsin daropate on monocyte proliferation.

Colforsin daropate is a water-soluble forskolin derivative, and acts as an adenyl cyclase activator with positive inotropic and vasodilatory effects that are useful in the treatment of ventricular dysfunction. However, there are no reports of its biological availability regarding inhibition of bone resorption and stimulation of bone formation. Preferably, the colforsin daropate of the present invention is able to inhibit osteoclast activity by blocking the RANKL-induced signal transduction pathway and promoting osteoblast activity by increasing alkaline phosphatase (ALP) activity. More preferably, the composition of the present invention is able to inhibit the TARP expression induced by RANKL, and enhance the synthesis of osteopontin, osteocalcin, or type I collagen that is induced by ALP. In addition, the composition of the present invention shows these effects without toxicity. In the preferred embodiment of the present invention, the treatment of monocytes with colforsin daropate showed no cytotoxicity at the active concentration (FIG. 1).

The pharmaceutical composition of the present invention includes colforsin daropate of Chemical Formula 1 as an active ingredient, and colforsin daropate used in the present invention may be easily prepared by those skilled in the art using a known preparation method or commercially available colforsin daropate may be used. In the present invention, a precursor of colforsin daropate, forskolin was preferably isolated and purified from a natural plant by a known preparation method (Shan Y, et al., Chem Pharm Bull (Tokyo). 2007, 55, 376-81.), and the isolated and purified forskolin was used to synthesize colforsin daropate by a known preparation method (Tatee T, et al., Chem Pharm Bull (Tokyo). 1996, 44, 2274-9.).

The pharmaceutical composition of the present invention may be used in the form of the colforsin daropate of Chemical Formula 1 or a pharmaceutically acceptable salt thereof. The salt useful in the present invention is an acid addition salt formed with a pharmaceutically acceptable free acid. An acid addition salt may be prepared using a common method, for example, by dissolving a compound in an excess amount of aqueous acid solution and precipitating the salt formed using a water-miscible organic solvent, such as methanol, ethanol, acetone or acetonitrile. Alternatively, an acid addition salt may be formed by heating an equimolar amount of a compound and an acid in water or alcohol (e.g., glycol monomethyl ether), and subsequently evaporating the mixture until dry or filtering the precipitated salt under suction. In this regard, the free acid may be an inorganic acid or an organic acid. Examples of the inorganic acids may include hydrochloric acid, phosphoric acid, sulfuric acid, nitric acid and stannic acid, and examples of the organic acids may include methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, and hydroiodic acid, but are not limited to.

In addition, a pharmaceutically acceptable metal salt may be prepared using a base. An alkali metal or alkaline earth metal salt may be obtained, for example, by dissolving a compound in an excess amount of alkali metal hydroxide or alkaline earth metal hydroxide solution, filtering the undissolved salt, and then evaporating the filtrate until dry. As the metal salts, sodium, potassium or calcium salts are pharmaceutically suitable, but the present invention is not limited thereto. Also, the corresponding silver salts may be obtained by reacting an alkali metal or alkaline earth metal salt with a proper silver salt (e.g., silver nitrate).

Pharmaceutically acceptable salts of colforsin daropate of Chemical Formula 1, unless otherwise indicated herein, include salts of acidic or basic groups, which may be present in the colforsin daropate of Chemical Formula 1. For example, the pharmaceutically acceptable salts may include sodium, calcium and potassium salts of hydroxy group, and other pharmaceutically acceptable salts of amino group, including hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate). The salts may be prepared using a salt preparation method known in the art.

The composition of the present invention may be used for bone diseases caused by the imbalance between osteoblasts and osteoclasts without limitation, and examples of the diseases include growth retardation, bone fracture, osteoporosis by excessive osteoclastic bone resorption, rheumatoid arthritis, periodontal disease, Paget's disease, and diseases caused by bone destruction resulting from pathological bone diseases such as metastatic cancers, but are not limited thereto.

As used herein, the term "prevention or treatment of bone diseases" includes prevention and complete or partial treatment of bone diseases, and also includes reduction and improvement in the symptoms of bone diseases, amelioration of the painful symptoms, reduction in the incidence rate of bone diseases or improvement in treatment results.

In one preferred embodiment, the composition of the present invention is characterized by inhibiting differentiation and bone resorption of osteoclasts.

As used herein, the term "osteoclast" refers to a cell derived from a macrophage precursor, and osteoclast precursors differentiate into osteoclasts in response to macrophage colony stimulating factor (M-CSF) and the receptor activator of NF-κB ligand (RANKL), and form multinucleated osteoclasts by fusion. Osteoclasts bind to bone through $\alpha v \beta 3$ integrin to create an acidic microenvironment, and release collagenase and protease to cause bone resorption. Osteoclasts are differentiated terminally, they do not proliferate, and they die by apoptosis after an estimated lifespan of about 2 weeks.

Figure 2:
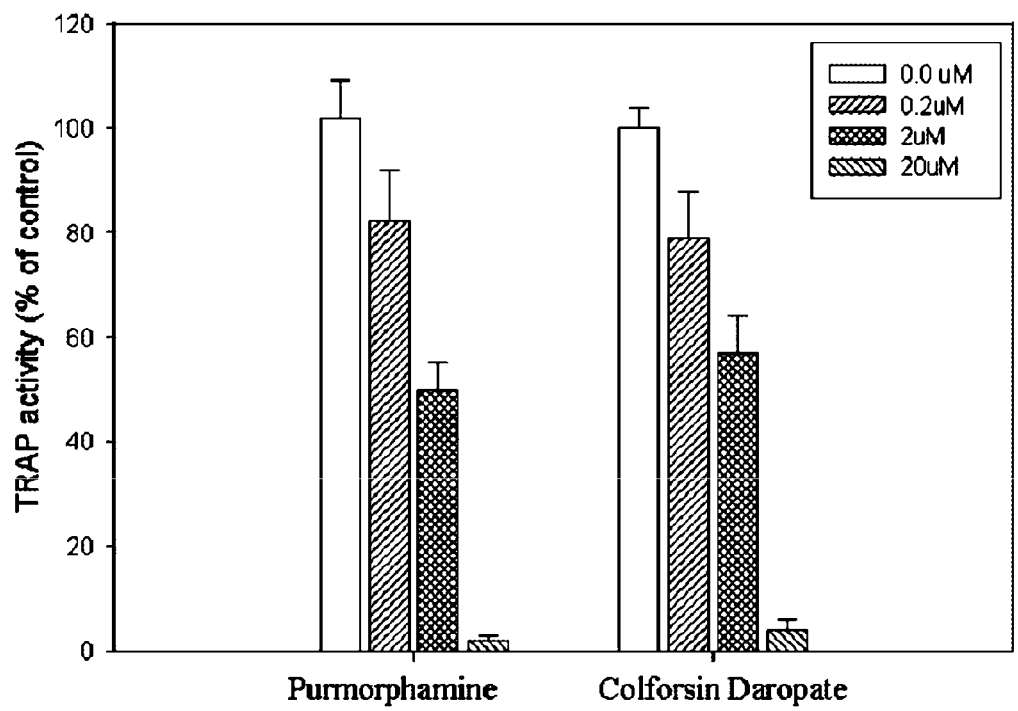
FIG. 2 is a graph showing that colforsin daropate inhibited the osteoclast differentiation marker, TRAP activity induced by RANKL.

In one preferred embodiment of the present invention, mouse monocytes that differentiate into osteoclasts were treated with the composition of the present invention, and then stained with an osteoclast differentiation factor, TRAP (tartrate-resistant acid phosphate). As a result, it was found that the composition of the present invention inhibited TRAP activity in a concentration-dependent manner (FIG. 2). As such, the composition of the present invention effectively inhibits osteoclast differentiation through inhibition of TRAP activity, thereby preventing or treating bone diseases caused by increased osteoclast activity, such as osteoporosis.

Further, the composition of the present invention is characterized by promoting the differentiation or activity of osteoblasts.

As used herein, the term "osteoblast" is a cell produced by the differentiation of mesenchymal stem cells, and functions to build bone to increase bone density. Occasionally, excessive osteoblast activity increases bone density, leading to bone malformation or osteopetrosis.

In the preferred embodiment of the present invention, when osteoblasts were treated with the composition including colforsin daropate, the activity of an early marker of osteoblast differentiation, ALP (alkaline phosphatase) was found to be remarkably increased (Example 3 and FIG. 3). In addition, when laboratory mice having reduced bone density by ovariectomy were orally administered with the colforsin of the present invention, the bone density was found to be remarkably increased (Example 4 and FIG. 4). The results suggest that the composition of the present invention is able to differentiate osteoblasts at a cell level, and also practically increase the bone density of animals, and thus support that the composition of the present invention promotes differentiation or activity of osteoblasts, thereby exhibiting prophylactic or therapeutic effects on bone diseases. The composition of the present invention is able to promote the synthesis of osteopontin, osteocalcin, and type I collagen by increasing ALP activity, and consequently promotes differentiation and activity of osteoblasts, thereby effectively preventing and treating diseases that are caused by inhibition of the differentiation and activity of osteoblasts.

Preferably, the pharmaceutical composition of the present invention may include colforsin daropate as an active ingredient in an amount of 0.0001 to 50% by weight, and more preferably 0.1 to 1% by weight, based on the total weight of the composition.

In one preferred embodiment, the pharmaceutical composition of the present invention may further include a pharmaceutically acceptable carrier. As the pharmaceutically acceptable carriers, a binder, a lubricant, a disintegrant, an excipient, a solubilizer, a dispersion agent, a stabilizer, a suspension agent, a pigment, and a flavor may be used for oral administration, and a buffer, a preserver, an analgesic agent, a solubilizer, an isotonic agent, and a stabilizer may be used in a mixed form for injective formulation, and a base, an excipient, a lubricant, and a preserver may be used for topical administration. The formulations of the pharmaceutical composition of the present invention may be prepared in various manners by mixing it with the pharmaceutically acceptable carriers as mentioned above. For example, for oral administration, it may be formulated into the form of a tablet, troche, capsule, elixir, suspension, syrup, wafer, etc. For injective formulation, it can be formulated into the form of a unit dosage ampoule or multi dosage forms. Alternatively, it may be formulated into a solution, a suspension, a tablet, a capsule, a sustained-release formulation, etc.

In this regard, examples of suitable carriers, diluents or excipients include excipients such as starch, sugar, and mannitol; fillers and bulking agents such as calcium phosphate and silicic acid derivatives; binding agents such as cellulose derivatives (e.g., carboxymethyl cellulose and hydroxypropyl cellulose), gelatin, alginate, and polyvinylpyrrolidone; lubricants such as talc, calcium or magnesium stearate, hydrogenated castor oil, and solid-phase polyethylene glycol; disintegrants such as povidone, croscarmellose sodium, and crospovidone; and surfactants such as polysorbate, cetyl alcohol, and glycerol monostearate.

In another embodiment, the present invention relates to a method for treating bone diseases, comprising the step of administering the pharmaceutical composition to an individual.

As used herein, the term "individual" encompasses mammals including mouse, livestock, and human, without limitation.

Further, the pharmaceutical composition according to the present invention may be administered via various routes. As used herein, the term "administration" means introduction of a predetermined amount of a substance into a patient by certain suitable method. The composition may be administered via any of the common routes, as long as the drug is able to reach a desired tissue. Specifically, a variety of administration modes are contemplated, including intraperitoneally, intravenously, intramuscularly, subcutaneously, intradermally, orally, topically, intranasally, intrapulmonarily and intrarectally, but the present invention is not limited to these exemplified administration modes. However, since peptides are digested upon oral administration, active ingredients of a composition for oral administration should be coated or formulated for protection against degradation in the stomach. Preferably, the present composition may be administered in an injectable form. In addition, the pharmaceutical composition of the present invention may be administered using a certain apparatus capable of transporting the active ingredients into a target cell.

In the present invention, the administration dose of the pharmaceutical composition including colforsin daropate may be determined by several related factors including the types of diseases to be treated, administration routes, the patient's age, gender, weight and severity of the illness, as well as by the types of the drug as an active ingredient. Preferably, colforsin daropate as an active ingredient may be administered into mammals including human at a daily dose of 1 to 20 mg/kg, and more preferably 1 to 10 mg/kg, which may be administered in a single dose or in divided doses.

In still another embodiment, the present invention relates to a health functional food composition for the prevention or amelioration of bone diseases, comprising the compound of Chemical Formula 1 or a sitologically acceptable salt thereof. When the composition of the present invention is used as a food additive, the colforsin daropate may be suitably used as it is or together with other foods or food ingredients according to a common method. A mixing amount of the active ingredient may be properly determined depending on the purpose (for prevention, health improvement, or therapeutic treatment).

As used herein, the term "health functional food" refers to a certain ingredient as a raw material or a food manufactured/processed by extraction, concentration, purification of a certain ingredient included in the food raw material for the purpose of health improvement, and refers to a food that is designed and processed to exhibit body modulating function such as body defense, regulation of biorhythm, and prevention and recovery of diseases. The above health functional food composition can perform the functions of preventing and recovering diseases.

Further, there is no particular limit to kinds of the health foods in which the composition of the present invention can be used. Furthermore, the composition including the colforsin daropate of the present invention as an active ingredient may be prepared by mixing it with auxiliary ingredients and the known additives that are appropriately selected by those skilled in the art. Examples of the food to be added include meat, sausage, bread, chocolate, candy, snack, cookie, pizza, instant noodle, other noodles, chewing gum, dairy products including ice cream, various kinds of soup, beverage, tea, drink, alcoholic beverages and vitamin complex, and the food may be prepared by adding the extract according to the present invention as a main ingredient to a squeezed liquid, tea, jelly, and juice.

MODE FOR INVENTION

Hereinafter, the present invention will be described in more detail with reference to the following Examples. However, these Examples are for illustrative purposes only, and the invention is not intended to be limited by these Examples.

Example 1

Cultivation of Monocytes and Cytotoxicity Test

The murine monocytic cell line, RAW264.7 (ATTC TIB-71) was cultured in a DMEM medium supplemented with 10% FBS, and the medium was replaced every other day. The cell culture reagents were purchased from Hyclone. When RAW264.7 cells reached 70% confluence, the collected cells were aliquotted into a 96-well plate at a density of $1 \times 10^3$/well, and cultured for 24 hours. Subsequently, the cells were treated with colforsin daropate at various concentrations (0, 10, 20 and 30 µM), and cultured for 96 hours. After 1, 2, and 4 days in culture, a cytotoxicity test was performed using the cells in each well and a CCK-8 kit (Dojindo, Japan).

As a result, colforsin daropate showed no cytotoxicity at the active concentration (FIG. 1).

Example 2

Osteoclast Differentiation, TRAP Staining and Activity Assay

When RAW264.7 cells reached 70% confluence, the collected cells were aliquotted into a 96-well plate at a density of $1 \times 10^3$/well. At this time, α-MEM containing 100 ng/ml RANKL (R&D systems) and 10% FBS was used as a cell suspension medium. After 24 hours, the cells were treated with colforsin daropate at various concentrations (0, 0.2, 1, 2, 10, and 20 µM). After 3 days, TRAP staining was performed using a leukocyte acid phosphatase kit (Sigma). The stained cells were first fixed in 10% formalin for 10 minutes, and then dehydrated in 95% ethanol, and dried well at room temperature. Subsequently, 100 µl of citrate buffer (50 mM, pH 4.6) containing 10 mM sodium tartrate and 5 mM p-nitrophenylphosphate was added to each well, and reacted for 20 to 30 minutes. Thereafter, the enzyme reaction mixtures were transferred into new 96-well plates, and the reaction was terminated using 100 µl of 0.1 N NaOH. Absorbance was measured at 405 nm. TRAP activity was presented as a % of control, and a significance test was performed by t-test at the same time (purmorphamine treatment $p<0.01$; colforsin daropate treatment $p<0.001$). Purmorphamine was used as a control compound.

As a result, it was found that colforsin daropate inhibited TRAP activity induced by RANKL in the monocytic cell line RAW264.7 in a concentration-dependent manner (FIG. 2). In addition, it can be seen that colforsin daropate showed an efficacy of inhibiting osteoclast differentiation without cytotoxicity (FIGS. 1 and 2).

Example 3

Assay for Alkaline Phosphatase (ALP) Activity of Osteoblast

In order to examine the effect of colforsin daropate on the activity of ALP, of which activity and expression are known to be increased at an early stage of osteoblast differentiation, the following experiment was performed.

A murine osteoblastic cell, MC3T3-E1 subclone 4 (ATCC CRL-2593) was treated with colforsin daropate. After 8 days, cells were lysed using a lysis buffer (10 mM Tris-HCl, pH 7.5, 0.5 mM $MgCl_2$, 0.1% Triton X-100) at room temperature for 30 minutes, and centrifuged at 12,000 rpm and 4° C. for 20 minutes. Next, ALP was quantified in the obtained supernatant using a BCA kit (Bio-Rad), and its activity was measured using a LabAssay ALP kit (Wako, Japan). In this regard, the measured activity was presented as a % of the control, and a significance test was performed by t-test (colforsin daropate treatment, $p<0.05$; purmorphamine treatment as control, $p<0.05$). The same experiment was performed using multipotent C3H10T1/2 cells (cells can differentiate toward various lineages, including osteocytes).

As a result, the activity of ALP, which is an early marker of osteoblast differentiation, was remarkably increased according to colforsin daropate treatment (FIG. 3A). The ALP activity was also remarkably increased in the multipotent C3H10T1/2 cells (FIG. 3B). The results demonstrate that colforsin daropate did not affect cell proliferation of the murine osteoblastic cell, MC3T3-E1 subclone 4, and more increased the osteoblast differentiation-related ALP activity at 1 mM concentration than the control compound, purmorphamine.

Example 4

Test of Bone Density-Improving Effect of Colforsin in Laboratory Animal

Many studies have been made in order to demonstrate the effects of osteoporosis therapeutic agents, but there are restrictions on clinical trials in humans. Thus, most studies are performed in animals. Ovariectomized mice are frequently used as a model for postmenopausal osteoporosis. Ovariectomized mice and early postmenopausal women share many similar characteristics, and thus ovariectomized mice have been commonly used in the studies of osteoporosis therapeutic agents. The present inventors performed ovariectomies on 5-week-old DDY female mice. The mice were anesthetized by intraperitoneal injection of 25 mg/kg of pentobarbital sodium (JW Pharmaceutical Corp). The abdomen of each mouse was shaved, and the surgical site was cleansed with antiseptics to perform ovariectomy. A 1.5 cm abdominal incision was made through the skin, muscle, and peritoneum to expose the ovary. The ovary was dissected out, and the peritoneum, muscle, and skin were sutured. As a control group, a sham ovariectomy was performed to the peritoneum identically, but the ovaries remained intact.

The mouse models having ovariectomy-induced bone loss were orally administered (p.o.) with the colforsin compound at the concentrations of 5 mg/kg or 10 mg/kg once a day for 4 weeks. The effects were examined using a high resolution in-vivo micro-CT system (explore Locus scanner, GE Health Care, USA) to analyze the bone density. As shown in FIG. 4, the ovariectomy-induced bone loss was found to be remarkably improved at 4 weeks after colforsin treatment.

What is claimed is:

1. A method for treating or ameliorating bone diseases, comprising administering a composition to an individual, wherein the composition comprises a compound represented by the following Chemical Formula 1 or a pharmaceutically acceptable salt thereof, wherein the bone disease is selected from the group consisting of osteoporosis, Paget's disease, periodontal disease, bone growth disorder, bone metastatic cancer, and rheumatoid arthritis

[Chemical Formula 1]

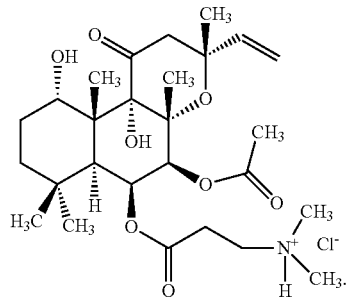

2. The method according to claim 1, wherein the composition inhibits differentiation or bone resorption of osteoclasts.

3. The method according to claim 1, wherein the composition promotes differentiation or activity of osteoblasts.

4. The method according to claim 1, wherein the composition further comprising a pharmaceutically acceptable carrier.

5. The method according to claim 1, wherein the compound represented by Chemical Formula 1 is included in an amount of 0.01 to 1% by weight.

* * * * *